(12) United States Patent
Ma et al.

(10) Patent No.: US 8,805,047 B2
(45) Date of Patent: *Aug. 12, 2014

(54) SYSTEMS AND METHODS FOR ADAPTIVE VOLUME IMAGING

(71) Applicant: FUJIFILM Sonosite, Inc., Bothell, WA (US)

(72) Inventors: Qinglin Ma, Kirkland, WA (US); Nikolaos Pagoulatos, Kirkland, WA (US)

(73) Assignee: FUJIFILM Sonosite, Inc., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/741,176

(22) Filed: Jan. 14, 2013

(65) Prior Publication Data

US 2013/0188832 A1 Jul. 25, 2013

Related U.S. Application Data

(63) Continuation of application No. 12/423,492, filed on Apr. 14, 2009, now Pat. No. 8,355,554.

(51) Int. Cl.
*G06K 9/00* (2006.01)

(52) U.S. Cl.
USPC ........................................................ 382/131

(58) Field of Classification Search
USPC ........................................................ 382/131
See application file for complete search history.

(56) References Cited

U.S. PATENT DOCUMENTS

| | | | |
|---|---|---|---|
| 5,603,318 A | 2/1997 | Heilbrun et al. | |
| 5,913,824 A | 6/1999 | Ogasawara et al. | |
| 6,048,312 A | 4/2000 | Ishrak et al. | |
| 6,216,029 B1 | 4/2001 | Paltieli | |
| 6,233,476 B1 | 5/2001 | Strommer et al. | |
| 6,317,621 B1 | 11/2001 | Graumann et al. | |
| 6,390,982 B1 | 5/2002 | Bova et al. | |

(Continued)

FOREIGN PATENT DOCUMENTS

| | | |
|---|---|---|
| CN | 1720464 | 1/2006 |
| EP | 1609424 | 12/2005 |

(Continued)

OTHER PUBLICATIONS

Merz, E. "Three-dimensional Ultrasound in the Evaluation of Fetal Anatomy and Fetal Malformations." Sonoace International Dec. 31, 1996, vol. 13, No. 4, pp. 23-36.

(Continued)

*Primary Examiner* — Rodney Fuller
(74) *Attorney, Agent, or Firm* — Perkins Coie LLP

(57) ABSTRACT

Systems and methods which provide volume imaging by implementing survey and target imaging modes are shown. According to embodiments, a survey imaging mode is implemented to provide a volume image of a relatively large survey area. A target of interest is preferably identified within the survey area for use in a target imaging mode. Embodiments implement a target imaging mode to provide a volume image of a relatively small target area corresponding to the identified target of interest. The target imaging mode preferably adapts the beamforming, volume field of view, and/or other signal and image processing algorithms to the target area. In operation according to embodiments, the target imaging mode provides a volume image of a target area with improved volume rate and image quality.

12 Claims, 3 Drawing Sheets

(56) References Cited

U.S. PATENT DOCUMENTS

| | | |
|---|---|---|
| 6,405,072 B1 | 6/2002 | Cosman |
| 6,490,477 B1 | 12/2002 | Zylka et al. |
| 6,511,426 B1 | 1/2003 | Hossack et al. |
| 6,591,130 B2 | 7/2003 | Shahidi |
| 6,611,141 B1 | 8/2003 | Schulz et al. |
| 6,790,181 B2 | 9/2004 | Cai et al. |
| 6,911,008 B2 | 6/2005 | Pelissier et al. |
| 6,951,542 B2 | 10/2005 | Greppi et al. |
| 7,270,634 B2 | 9/2007 | Scampini et al. |
| 7,338,448 B2 | 3/2008 | Hao et al. |
| 7,346,228 B2 | 3/2008 | Sabourin et al. |
| 7,386,339 B2 | 6/2008 | Strommer et al. |
| 7,601,121 B2 | 10/2009 | Pagoulatos et al. |
| 7,658,713 B2 | 2/2010 | Barnes et al. |
| 7,925,068 B2 | 4/2011 | Hoctor et al. |
| 8,088,071 B2 | 1/2012 | Hwang et al. |
| 8,147,408 B2 | 4/2012 | Bunce et al. |
| 8,355,554 B2 * | 1/2013 | Ma et al. .................. 382/131 |
| 2002/0049375 A1 | 4/2002 | Strommer et al. |
| 2002/0165448 A1 | 11/2002 | Ben-Haim et al. |
| 2002/0173719 A1 | 11/2002 | Zhao et al. |
| 2003/0050557 A1 | 3/2003 | Susil et al. |
| 2003/0130576 A1 | 7/2003 | Seeley et al. |
| 2003/0135119 A1 | 7/2003 | Lee et al. |
| 2003/0220559 A1 | 11/2003 | Ehnholm et al. |
| 2005/0002570 A1 | 1/2005 | Clark et al. |
| 2005/0008254 A1 | 1/2005 | Ouchi et al. |
| 2005/0096538 A1 | 5/2005 | Chomas et al. |
| 2005/0215893 A1 | 9/2005 | Barnes et al. |
| 2006/0098853 A1 | 5/2006 | Roundhill et al. |
| 2006/0241432 A1 | 10/2006 | Herline et al. |
| 2007/0016039 A1 | 1/2007 | Vortman et al. |
| 2007/0073136 A1 | 3/2007 | Metzger |
| 2007/0100234 A1 | 5/2007 | Arenson et al. |
| 2007/0193354 A1 | 8/2007 | Felix et al. |
| 2008/0021300 A1 | 1/2008 | Allison |
| 2008/0077009 A1 | 3/2008 | Lee et al. |
| 2008/0119735 A1 | 5/2008 | Lin et al. |
| 2008/0183079 A1 | 7/2008 | Lundberg |
| 2008/0221425 A1 | 9/2008 | Olson et al. |
| 2008/0242968 A1 | 10/2008 | Claus et al. |
| 2008/0269610 A1 | 10/2008 | Burla et al. |
| 2009/0264760 A1 | 10/2009 | Lazebnik et al. |
| 2010/0121189 A1 | 5/2010 | Ma et al. |
| 2010/0121190 A1 | 5/2010 | Pagoulatos et al. |
| 2011/0249878 A1 | 10/2011 | Pagoulatos et al. |

FOREIGN PATENT DOCUMENTS

| | | |
|---|---|---|
| WO | WO-2006089426 | 8/2006 |
| WO | WO-2010135035 | 11/2010 |
| WO | WO-2011127191 | 10/2011 |

OTHER PUBLICATIONS

Merz, E. et al. Internet excerpt from "Volume Scanning in the Evaluation of Fetal Malformations: A New Dimension in Prenatal Diagnosis," Journal of Ultrasound in Obstetrics and Gynecology, vol. 5, 1995, pp. 222-227 (excerpt, 3 pages).

International Search Report and Written Opinion, PCT Application PCT/US2010/030058, mailed Jul. 9, 2010, 11 pages.

International Search Report and Written Opinion, PCT Application PCT/US2009/062987, mailed Mar. 19, 2010, 11 pages.

International Search Report and Written Opinion, PCT Application PCT/US2009/062976, mailed Jan. 7, 2010, 11 pages.

International Search Report and Written Opinion, PCT Application PCT/US2011/031447, mailed Jun. 21, 2011, 9 pages.

Non- Final Office Action for CN Patent Application No. 201080026281.8, mailed Jul. 3, 2013; 13 pages.

Non-Final Office Action for U.S. Appl. No. 12/790,109, mailed Aug. 19, 2013; 25 pages.

Ding et al. "A real-time biopsy needle segmentation technique using Hough transform." Medical Physics vol. 30; Published Jul. 23, 2003; 12 pages.

Barrett et al. "Object-based image editing" ACM Trans.Published Jul. 2002; 8 pages.

Smith, Alvy Ray. "Image Compositing Fundamentals." Technical Memo 4; Published Aug. 15, 1985; 8 pages.

European Patent Office, European Extended Search Report, EP Patent Application 10778075.1, Nov. 25, 2013, 8 pages.

* cited by examiner

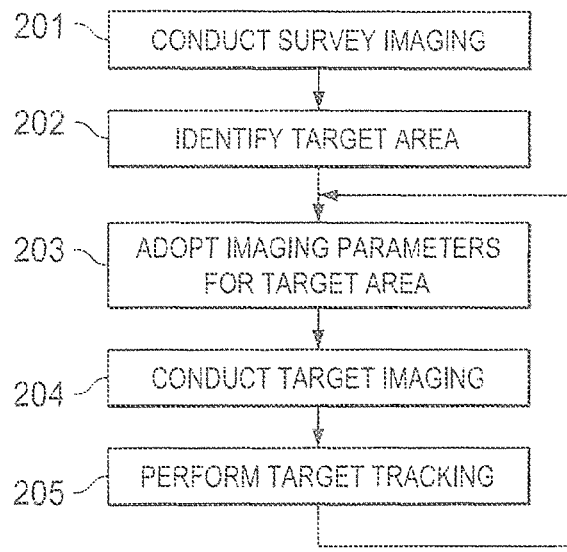
FIG. 2
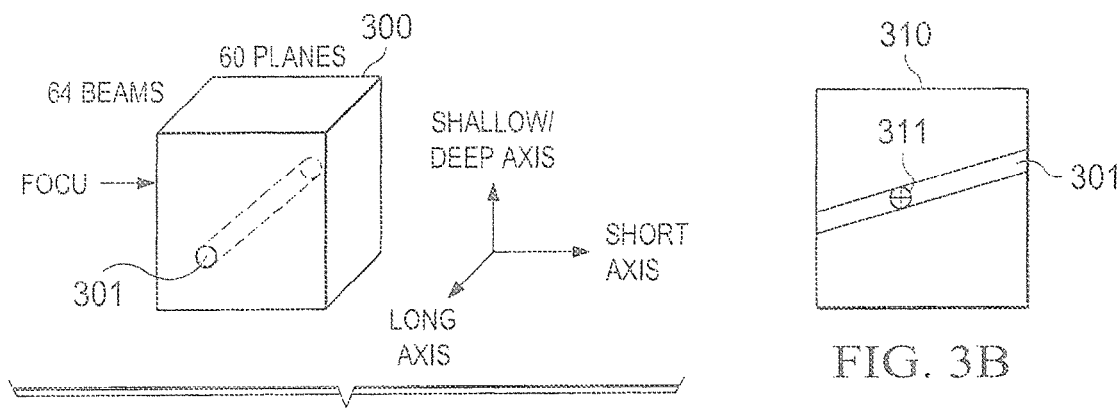
FIG. 3A
FIG. 3B
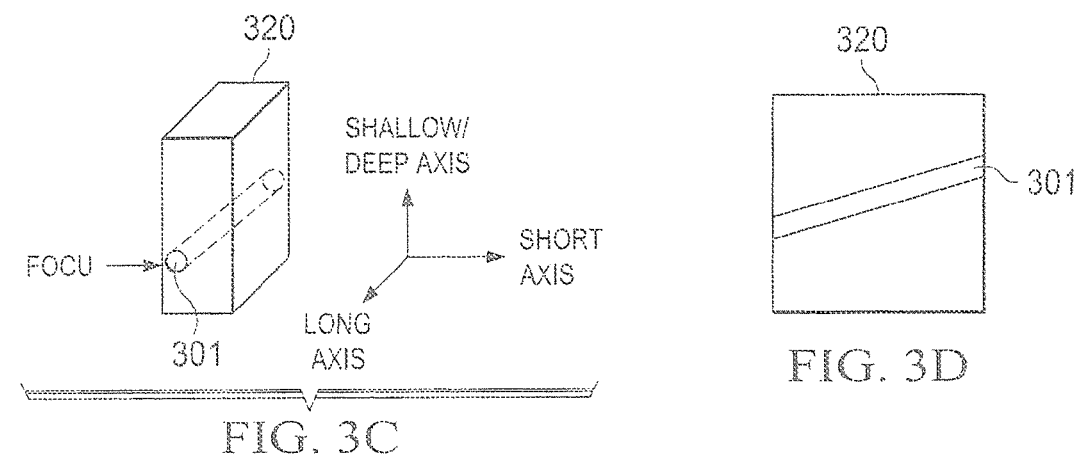
FIG. 3C
FIG. 3D

SYSTEMS AND METHODS FOR ADAPTIVE VOLUME IMAGING

CROSS-REFERENCE TO RELATED APPLICATIONS

The present application is a continuation of U.S. patent application Ser. No. 12/423,492 entitled "Systems and Methods for Adaptive Volume Imaging", filed Apr. 14, 2009, now U.S. Pat. No. 8,355,554, the entirety of which is hereby incorporated herein by reference. The present application is also related to co-pending and commonly assigned U.S. patent application Ser. No. 12/269,623 entitled "Systems and Methods for Image Presentation for Medical Examination and Interventional Procedures," filed Nov. 12, 2008, and Ser. No. 12/269,663 entitled "Systems and Methods to Identify Interventional Instruments," filed Nov. 12, 2008, the disclosures of which are hereby incorporated herein by reference.

TECHNICAL FIELD

The invention relates generally to volume imaging and, more particularly, to providing adaptive volume imaging.

BACKGROUND OF THE INVENTION

Various forms of imaging apparatus have been used extensively for medical applications. For example, fluoroscope systems, X-ray imaging systems, ultrasound imaging systems, computed tomography (CT) imaging systems, and magnetic resonance (MR) imaging (MRI) systems have been used for a number of years. Any number of medical examination, interventional procedures, diagnosis, and/or treatment may be provided using an appropriate one of the foregoing systems suited for the task.

Ultrasound imaging systems have been used as a tool for assisting interventional clinical procedures and medical examinations. For example, conventional two-dimensional (2D) ultrasound imaging has been used in the field of regional anesthesia to provide a way of "seeing" and tracking the delivery of the anesthetic with a needle, rather than attempting to achieve such a goal blindly using nerve stimulation technology. Additionally, 2D ultrasound imaging has been used by medical practitioners for examination of various regions of interest within a patient's body, such as to view anatomical structures (e.g., cardiac, pulmonary, gastrointestinal, and other structures), in utero fetuses, tumors, and the like.

Ultrasound imaging technology has developed to a point that high quality 2D images are provided and image frame rates are relatively high. For example, transducer arrays are often used to sweep ultrasonic beams across an image plane to form high quality images. Various processing techniques have been developed to reduce speckle, sharpen edges, etc. However, the planar, vertical "slice" views typically provided by such 2D ultrasound imaging has not always provided practitioners with a desired view of the target. For example, particular structure of interest is often difficult to identify from a planar slice through that structure. Often, a view of a surface of a target structure is desired, which is often impossible or very difficult using traditional 2D ultrasound imaging techniques.

Computing technology, having progressed dramatically in the last few decades, has provided the ability to produce three-dimensional (3D) (e.g. a dataset providing information in an X, Y, and Z axes space) and even four-dimensional (4D) (e.g., a 3D image having a time axis added thereto) volume images. Ultrasound volume imaging (3D, 4D, real-time 3D, etc.) has seen increasing use with respect to medical procedures and medical examinations, especially OB/GYN and cardiac examinations. An advantage of volume imaging, is that with volume imaging it is possible to generate views of a region or target of interest, such as baby face and heart chambers, which are readily recognizable to the user. Using volume imaging techniques it is possible to reconstruct and visualize any arbitrary plane or even surface within the image volume that is not otherwise obtainable by 2D imaging.

However, the 3D and 4D imaging technology typically used in volume imaging arose from disciplines such as drafting, modeling, and even gaining, thus the technology has primarily been adopted for use in the medical field rather than having been developed uniquely for use in the medical field. Similarly, imaging transducer technology used with respect to 3D and 4D imaging (e.g., single beam mechanical single beam wobbler ultrasound transducers and matrix array ultrasound transducers) has primarily been adopted from 2D transducer technology. A disadvantage of volume imaging is its much slower volume rate compared to 2D imaging frame rates. For example, the volume rate in volume imaging is often limited by the size of the volume, acoustic imaging rate, and ultrasonic beam sweeping rate (e.g., the mechanical moving rate for a wobbler probe or the beam forming rate of a matrix array). Moreover, volume imaging techniques often suffer from degraded image quality for any arbitrary plane, especially the elevation plane if the volume is obtained by a wobbler transducer. For example, image quality is often limited, when a wobbler transducer is used, by a single-element beam providing poor sampling of the elevation plane and, when a matrix array transducer is used, by the limited number of elements of the matrix array (e.g., 32 to 64 compared to 128 to 256 elements for standard array transducer) and sparse beams in 3D space.

BRIEF SUMMARY OF THE INVENTION

The present invention is directed to systems and methods which provide volume imaging by implementing survey and target imaging modes. According to embodiments of the invention, a survey imaging mode is implemented to provide a volume image of a relatively large survey area. An area, point, or item (collectively referred to as a target) of interest is preferably identified within the survey area for use in a target imaging mode. Embodiments of the invention implement a target imaging mode to provide a volume image of a relatively small target area corresponding to the identified target of interest. The target imaging mode preferably adapts the beamforming, volume field of view, and/or other signal and image processing algorithms to the target area. In operation according to embodiments of the invention, the target imaging mode provides a volume image of a target area with improved volume rate and image quality.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which:

FIG. 2 shows a flow diagram of operation according to embodiments of the invention;

FIGS. 3A and 3B show operation of a survey imaging mode according to embodiments of the invention; and FIGS. 3C and 3D show operation of a target imaging mode according to embodiments of the invention.

DETAILED DESCRIPTION OF THE INVENTION

Figure 1A:
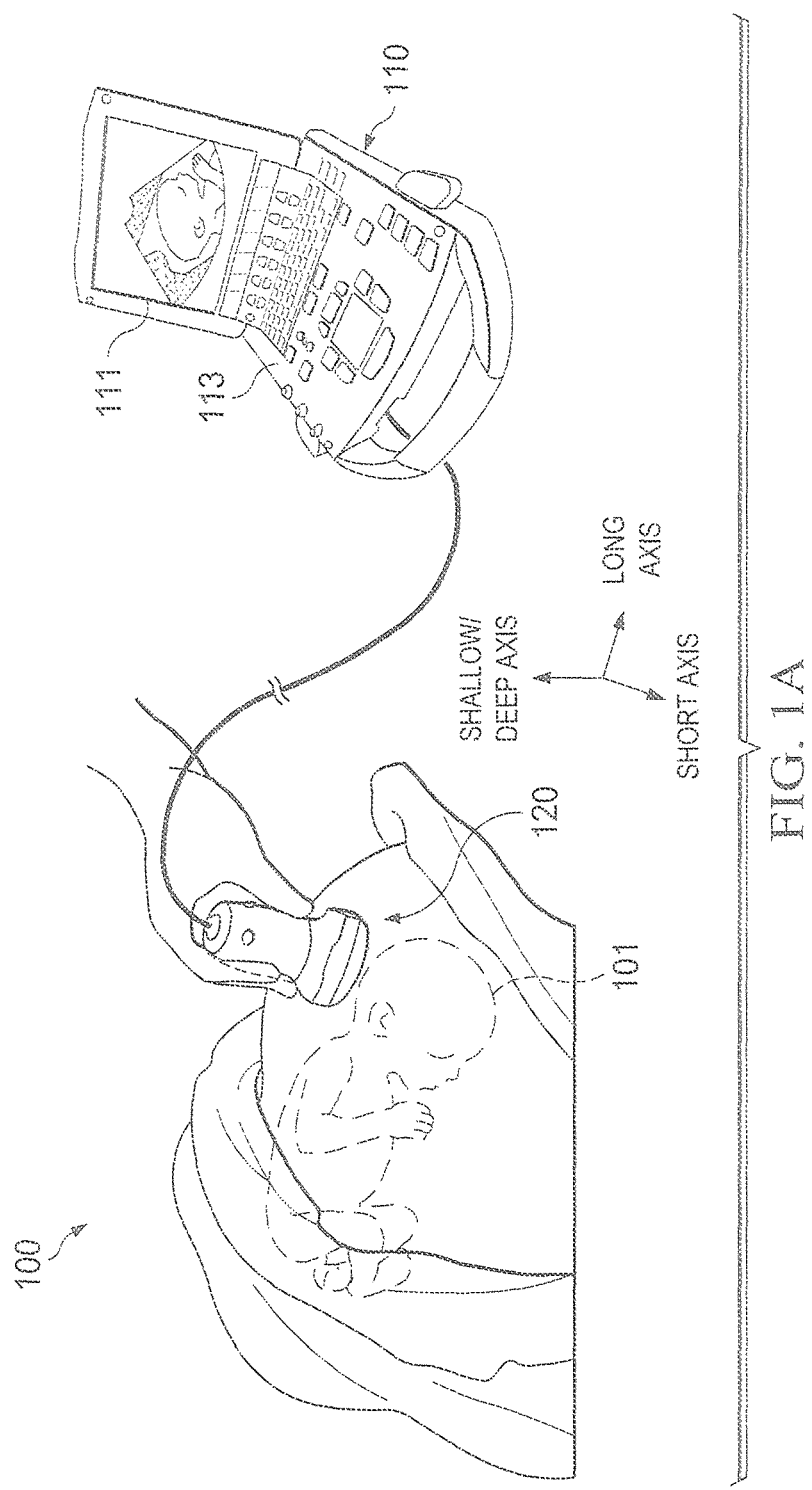
FIG. 1A shows a system adapted according to embodiments of the invention.

Directing attention to FIG. 1, a system adapted according to embodiments of the invention is shown as system 100. System 100 may, for example, comprise a diagnostic ultrasound system operable to provide 2D and/or 3D images from a multi-dimensional (e.g., 3D and/or 4D) volume dataset. Although embodiments of the invention are described herein with reference to ultrasound imaging technology, in order to aid the reader in understanding the invention, it should be appreciated that the concepts of the present invention are not limited in applicability to ultrasound imaging. For example, embodiments of the present invention may be implemented with respect to fluoroscope systems, X-ray imaging systems, ultrasound imaging systems, CT imaging systems, MRI systems, positron emission tomography (PET) imaging systems, and the like.

System 100 of the illustrated embodiment includes system unit 110 and transducer 120 coupled thereto. System unit 110 preferably comprises a processor-based system, such as shown in the high level block diagram of FIG. 1B. Transducer 120 may comprise a transducer configuration corresponding to the imaging technology used.

Figure 1B:
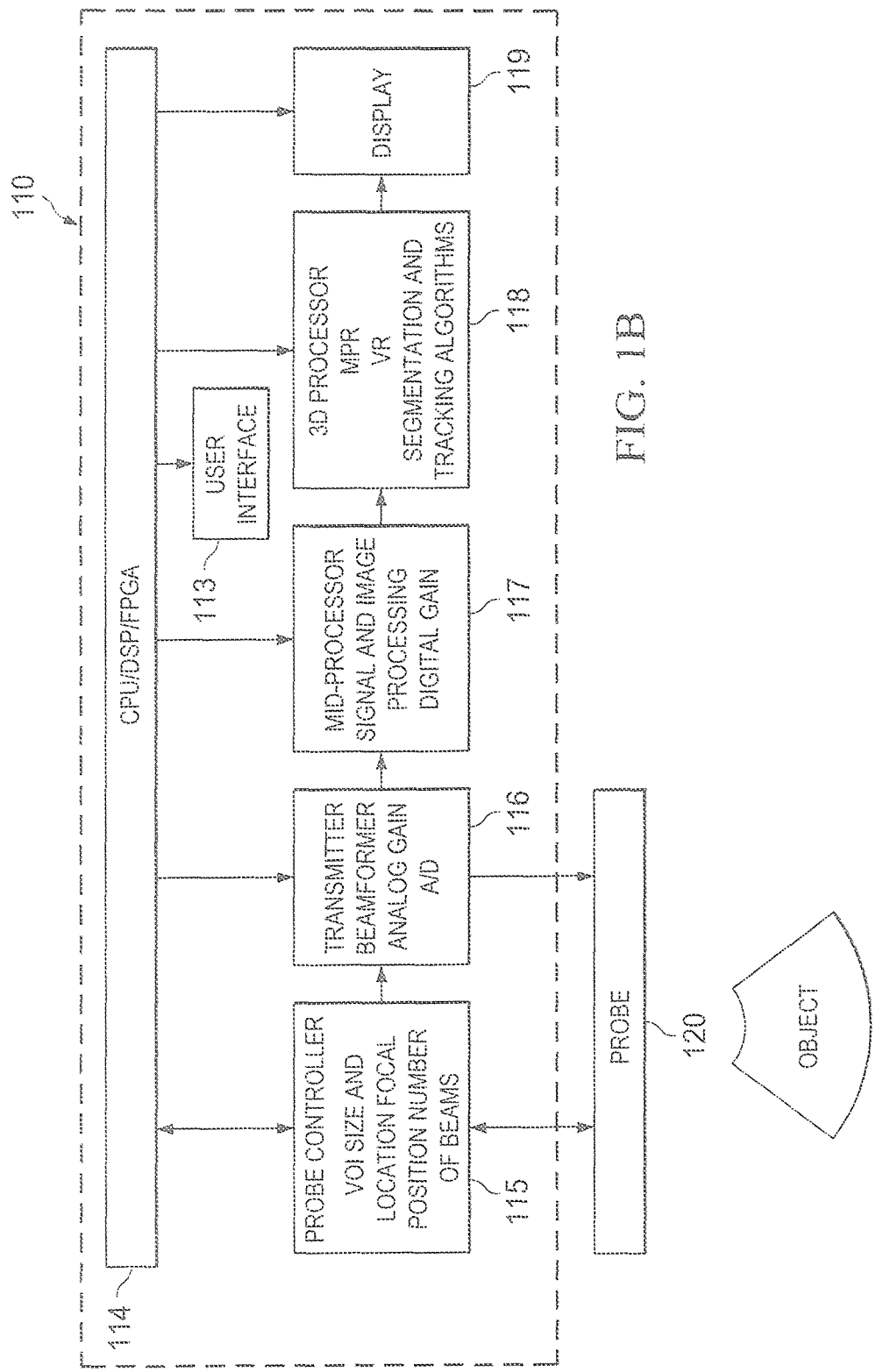
FIG. 1B shows a functional block diagram of embodiments of the system of FIG. 1A.

System unit 110 illustrated in FIG. 1B includes processor 114, such as may comprise a central processing unit (CPU), digital signal processor (DSP), field programmable gate array (FPGA), and/or the like, preferably having memory associated therewith. In embodiments, the processor-based system of system unit 110 may comprise a system on a chip (SOC), for example. Probe controller 115 of system unit 110 shown in FIG. 1B provides image dataset collection/acquisition control, such as to control the volume of interest size and location, the volume rate, the number of imaging slices used for image acquisition. etc. in both the survey imaging mode and the target imaging mode of embodiments of the invention. Front-end circuitry 116 of the illustrated embodiment provides signal transmission to drive probe 120, beamforming for transmission and/or reception of ultrasonic pulses, signal conditioning such as filtering, gain control (e.g., analog gain control), etc. Mid-processor 117 of the illustrated embodiment, operable under control of processor 114, provides signal and image processing, additional signal conditioning such as gain control (e.g., digital gain control), decimation, low-pass filtering, demodulation, re-sampling, lateral filtering, compression, amplitude detection, blackhole filling, spike suppression, frequency compounding, spatial compounding, decoding, and/or the like.

According to the illustrated embodiment, signals processed by mid-processor 117 are provided to back-end processor 118 for further image processing. Back-end processor 118 of embodiments preferably includes a 3D processor, and may additionally include a 2D processor. A 3D processor of back-end processor 118 may operate under control of processor 114 to produce 3D image volumes and images therefrom (e.g., MPR images, VR images) in both a survey imaging mode and a target imaging mode for presentation by display system 119 as image 111. The 3D processor of embodiments may further provide for image volume segmentation, image plane determination, target tracking, gray mapping, tint mapping, contrast adjustment, MPR generation, volume rendering, surface rendering, tissue processing, flow processing, etc. A 2D processor of back-end processor 118 may operate under control of processor 114 to provide scan control, speckle reduction, spatial compounding, and/or the like.

User interface 113 of embodiments may comprise keyboards, touch pads, touch screens, pointing devices (e.g., mouse, digitizing tablet, etc.), joysticks, trackballs, spinner knobs, buttons, microphones, speakers, display screens (e.g., cathode ray tube (CRT), liquid crystal display (LCD), organic LCD (OLCD), plasma display, back projection, etc.), and/or the like. User interface 113 may be used to provide user control with respect to multi-dimensional image mode selection, target area selection, image volume scanning, object tracking selection, depth selection, gain selection, image optimization, patient data entry, image access (e.g., storage, review, playback, etc.), and/or the like. Display system 119, comprising a part of user interface 113 of embodiments of the invention, preferably includes a video processor and display. A video processor of display system 119 may provide video processing control such as overlay control, gamma correction, etc. A display of display system 119 may comprise the aforementioned CRT, LCD, OLCD, plasma display, back projection display, etc. for displaying images, such as image 111.

Logic of system unit 110 preferably controls operation of system 100 to provide various imaging functions and operation as described herein. Such logic may be implemented in hardware, such as application specific integrated circuits (ASICs) or FPGAs, and/or in code, such as in software code, firmware code, etc.

According to a preferred embodiment, transducer 120 comprises one or more transducer elements and supporting circuitry to illuminate (e.g., insonify) a target, capture data (e.g., ultrasound echos), and provide target data (e.g., transducer response signals) to system unit 110 for use in imaging. Transducer 120 of the embodiment illustrated in FIG. 1B may, for example, comprise any device that provides conversion between some form of energy and acoustic energy, such as a piezoelectric transducer, capacitive micro-machined ultrasonic transducer (CMUT), a piezoelectric micro-machined ultrasonic transducer (PMUT), etc. Embodiments of transducer 120 comprise a mechanically moving 1D array (wobbler), single element probe, annular array, a matrix probe, CMUT array, and/or the like. Transducer 120 may be adapted for particular uses, procedures, or functions. For example, transducers utilized according to embodiments of the invention may be adapted for external use (e.g., topological), internal use (e.g., esophageal, vessel, rectal, vaginal, surgical, intravascular, etc.), cardio analysis, OB/GYN examination, etc.

It should be appreciated that, although the embodiment illustrated in FIG. 1B shows one particular division of functional blocks between system unit 110 and transducer 120, various configurations of the division of functional blocks between the components of system 100 may be utilized according to embodiments of the invention. For example, beamformer 116 may be disposed in transducer 120 according to embodiments of the invention. Moreover, although a particular combination of functional blocks are shown to comprise system unit 110 of the illustrated embodiment, it should be appreciated that functions performed by embodiments of the invention may be provided by one or more system units. For example, traditional image data collection and processing functions may be provided by an imaging system unit, such as a portable ultrasound system, and extended image processing functions according to embodiments of the invention may be provided by one or more system unit (e.g. an external personal computer (PC) system unit) in communication therewith.

In the illustrated embodiment, system 100 is being used with respect to an examination. Specifically, transducer 120 is being held against object 101, such as may comprise a portion of a human body, to illuminate an area of interest, such as may comprise an in utero fetus. It should be appreciated that volume imaging provided according to the concepts of the present invention may be utilized with respect to procedures in addition to or in the alternative to examinations, such as interventional procedures, diagnostic procedures, therapeutic procedures, etc.

Irrespective of the particular underlying procedure being performed, an image, shown as image 111, is preferably generated by system unit 110 to visually depict the insonified area in accordance with an imaging mode then active with respect to system unit 110. In providing the foregoing image, system unit 110 of embodiments may provide various signal and/or image processing techniques, such as tissue harmonic imaging (THI), demodulation, filtering, decimation, interpretation, amplitude detection, compression, frequency compounding, spatial compounding, black hole fill, speckle reduction, etc. Image 111 may comprise various forms or modes of images, such as color images, B-mode images, M-mode images, Doppler images, still images, cine images, live images, recorded images, etc. Regardless of the image generation techniques used, operation in accordance with the concepts of the present invention preferably provides volume imaging with improved volume rate and image quality adapted to the region or target of interest.

Thus, in operation according to embodiments, transducer 120 transmits ultrasound waves into an object, such as a human body, and receives a backscattered signal. Probe controller 115 determines the volume size, location (center of the imaging plane and volume boundary), focal zone location, the number of beams per image plane or the entire volume, etc. Front-end circuitry 116 generates electrical waves to drive transducer 120, and the beamformer of front-end circuitry 116 provides delays and weights to steer and focus transmit and receive beams which could be parallel beams per transmit beam. Mid-processor 117 provides signal and image processing such as quadrature detection, synthetic aperture, down sampling, interpretation (e.g., in both radio frequency (RF) and video domain), low pass filtering, digital gain, log compression, amplitude detection, black hole fill, noise spike filtering, speckle reduction, etc. back-end processor 118 provides 3D scan conversion, such as to form arbitrary plane images (MPR), to render volume or surface images. Target specific segmentation and tracking algorithms are preferably implemented by mid-processor 117 and/or back-end processor 118. User interface 113, such as may comprise a keyboard, mouse, hard or soft touch button, rotator, knobs, joystick, voice control, etc., provides a means for the user to interact with system 100 to optimize the MPR and VR image, interrogate and edit the volume, communicate to the system where the target is, how large a volume is needed, choose various display methods, and/or the like. Display system 119, such as may comprise a display screen (e.g., LCD, Plasma, CRT, etc.), headmount, hologram, stereo or virtual reality display device, provides display of generated images and other information. Communication, timing synchronization, and control with respect to the foregoing components is provided by a single or multiple CPU, DSP, FPGA or other device.

Directing attention to FIG. 2, a flow diagram showing operation of system 100 to provide volume imaging in accordance with an embodiment of the invention is shown. In accordance with the illustrated embodiment, system 100 is operated in a survey imaging mode to provide volume imaging with a wide field of view at block 201. Such a survey imaging mode preferably provides a "normal" or non-enhanced volume image using typical volume imaging techniques. Operation of a survey imaging mode to provide volume imaging with a wide field of view is represented by the volume image shown in FIG. 3A.

In the embodiment illustrated in FIG. 3A, 64 beams are directed at different angles along the long axis of transducer 120 to form an image plane, and 60 such image planes spaced along the short axis of transducer 120 are generated. The focal depth may be selected arbitrarily, such as to select a generally acceptable focal depth, a default focal depth, a last used focal depth, etc. Alternatively, the focal depth may be selected based upon one or more criteria, such as to select a focal depth typically utilized with respect to a particular procedure, a focal depth associated with a particular type of target, a focal depth for which a highest quality volume image is typically generated, etc. Of course, different numbers of beams and image planes and different focal depths may be utilized according to embodiments of the invention. However, the foregoing example is representative of the image quality provided by typical volume imaging techniques.

The foregoing survey imaging mode is preferably utilized to provide an expedient means by which to locate a target area (e.g., a particular target anatomy, an area of interest, an interventional tool, etc.). For example, a user may wish to view a particular target anatomy and may be unable to initially place transducer 120 precisely in relation to this target anatomy. Accordingly, using the wide field of view provided by the aforementioned survey imaging mode, the user may be able to place transducer 120 with sufficient precision to illuminate the target anatomy, or a portion thereof, within the survey imaging mode wide field of view. Thus, although the image quality and image rate provided by the survey imaging mode may be less than desired, the user may nevertheless be able to locate the target anatomy using the survey imaging mode.

For example, survey volume image dataset 300 generated using the survey imaging mode at block 201 may include target 301, perhaps along with other features, structures, etc., within its wide field of view as shown in FIG. 3A. It should be appreciated that a volume image generated using survey volume image dataset 300 may be displayed using display system 119 (e.g., as image 111). In this example it will be assumed that target 301 comprises a target anatomy, such as a blood vessel. However, it should be appreciated that target

301 may comprise various things, including one or more target anatomy, area of interest, interventional tool, etc.

At block 202 of the illustrated embodiment, a target of interest (e.g., area, point, or item) is identified within the volume image provided by the survey imaging mode. Embodiments of the invention may operate to identify such a target of interest within a volume image dataset automatically, such as using algorithms to recognize one or more feature within an image. Detail with respect to systems and methods for providing automated identification of targets and other areas of interest within a volume image dataset are shown and described in the above referenced patent application entitled "Systems and Methods to Identify Interventional Instruments." Additionally or alternatively, embodiments of the invention may be operated to identify such a target of interest within a volume image dataset manually, such as through a user manipulating a pointing device, touch screen, or other appropriate user interface.

The foregoing target identification, whether manual or automated, may be facilitated through the use of image presentation techniques adapted to facilitate readily interpreting the image and/or performing the desired task. Various such techniques which may be utilized with respect to target and area of interest identification are shown an described in the above referenced patent application entitled "Systems and Methods for Image Presentation for Medical Examination and Interventional Procedures." For example, the techniques for generating image planes from a volume image dataset (image volume segmentation) as shown in the foregoing patent application may be utilized to facilitate target identification at block 202 of embodiments of the invention.

Directing attention to FIG. 3B, an image plane generated from survey volume image dataset 300 (here a cross-sectional image generated along the long axis of transducer 120) and including at least a portion of target 301 is shown as image plane 310. It should be appreciated that image plane 310 may be displayed using display system 119 (e.g., as image 111). Image plane 310 may be utilized at block 202 of embodiments of the invention for identifying target 301. For example, algorithms of system 100 may step through image planes generated from survey volume image dataset 300 to identify one or more features of target 301 therein. Additionally or alternatively, a user may view image planes generated from survey volume image dataset 300 to identify target 301 therein. As shown in the illustrated embodiment, target 301 may be selected within an appropriate image, such as through use of curser 311. Such identification may comprise selecting the target within the image volume, defining an area of interest (e.g. location and size), etc.

At block 203 of the illustrated embodiment, imaging parameters of system 100 are adapted, such as by probe controller 115, for imaging the selected target of interest. For example, a determination may be made based upon the selected target of interest as to a new volume size for the image volume. Imaging parameters may correspondingly be adjusted to narrow the field of view. Similarly, imaging parameters may be adjusted to center the image volume field of view for the selected target of interest, to adjust the focal depth for the selected target of interest, to implement particular signal and/or image processing algorithms appropriate to the selected target of interest, etc. According to embodiments of the invention, the beam density used in generating the volume image is increased with respect to the selected target of interest. Additionally or alternatively, signal or image processing that enhances the image appearance, such as resolution and contrast for a particular target, may be applied according to an embodiment of the invention.

For example, imaging parameters are selected such that the beamformer of a matrix transducer steers the beams to cover only the area of interest according to an embodiment of the invention. Similarly, the wobbling angle of a wobbler transducer is decreased and the center of the wobbling field is changed in correspondence to a selected area of interest according to an embodiment. Additionally or alternatively, embodiments move the transmit focus or focal depth to the area of interest.

At block 204 of the illustrated embodiment, system 100 is operated in a target imaging mode to provide volume imaging with a narrow field of view. Such a target imaging mode preferably provides an enhanced volume image which provides improved image quality with respect to the selected target of interest. Accordingly, imaging parameters adapted for target imaging at block 203 are preferably implemented by system 100 in the target imaging mode of block 204. Operation of a target imaging mode to provide volume imaging with a field of view adapted for a selected target is represented by the volume image shown in FIG. 3C.

Target volume image dataset 320, which includes target 301 and may include other features, structures, etc., is generated using the target imaging mode according to embodiments of the invention as shown in FIG. 3C. Target volume image dataset 320 may, for example, be generated using 128 beams directed at different angles along a 10° region of the long axis of transducer 120 to form an image plane, and 20 such image planes spaced along the short axis of transducer 120. Of course, different numbers of beams and image planes may be utilized according to embodiments of the invention. However, the foregoing example is representative of a configuration providing improved image quality and relatively fast image rates in accordance with embodiments of the invention.

Various imaging parameters adapted for providing volume imaging of target 301 are implemented by system 100 in generating target volume image dataset 320. For example, target volume image dataset 320 is adjusted to substantially center target 301 within the field of view. Moreover, as can be seen in FIG. 3C, the focal depth has been adjusted to correspond with the depth of target 301. Adaptations other than those shown in FIG. 3C may additionally or alternatively be made, such as to orient target volume image dataset 320 to correspond to an orientation of target 301, to implement particular signal and image processing, etc. It should be appreciated that the foregoing adaptation of the imaging parameters in accordance with embodiments of the invention facilitates improved image quality with respect to the selected target of interest, while providing increased or otherwise acceptable image rates.

The foregoing target imaging mode is preferably utilized to provide display of the selected target of interest for use by a users (e.g., clinician, physician, sonographer, technician, patient, etc.) in various examinations, procedures, diagnosis, and/or the like. Such display may be provided as a volume image (e.g., 3D or 4D view), in an image plane (e.g., 2D view) such as image plane 330 of FIG. 3D, and/or the like. The improved image quality facilitated through the use of increased beam density, reduced field of view, and adaptation of image parameters provides images of a selected target of interest with desired clarity and detail previously unavailable in volume images. Moreover, the image rates attainable with a target image volume of embodiments of the invention facilitates 4D or moving images which are updated rapidly, even in near real-time according to embodiments of the invention. Accordingly, although image plane 330 of FIG. 3D appears in the illustration substantially similar to image plane 310 of FIG. 3B, it should be appreciated that image plane 330 represents an image having a higher refresh rate and better image quality.

It should be appreciated that the selected target of interest, the object hosting the selected target (e.g., the human body being examined), and/or the transducer used in acquiring the volume image dataset may move or otherwise change during imaging operations (e.g., during 4D imaging). Accordingly, block 205 of the illustrated embodiment performs target tracking to facilitate dynamic adaptation of imaging parameters and updated target imaging. For example, in 3D, live 3D imaging or 4D imaging mode, system 100 of a preferred embodiment will operate to lock on to the selected target of interest.

Tracking in accordance with embodiments may be done manually or automatically. In the case of manual tracking, the user may update the system as to where the target is by clicking on the target or using other user interface means. A user may, for example, manually indicate a change in size of the target area, a change in orientation of the target image volume field of view, a change in location of a selected target area, etc., such as using the aforementioned user interfaces. Preferably an automatic tracking method could be used to identify the target and lock the system on to it. For example, algorithms of system 100 may operate to automatically track target 301 for updating imaging parameters and provide updated target volume images. According to embodiments of the invention, logic of system 100 may continuously operate to segment the target volume image dataset and calculate the position of target 301 therein for near real-time updating the image, such as by continuing to use information identifying the target, tracking or updating previously identified putative locations of the target, using frame-to-frame image comparisons, and/or the like. Detail with respect to techniques for providing such automated tracking as may be implemented according to embodiments of the invention is provided in the above referenced patent application entitled "Systems and Methods to Identify Interventional Instruments."

Irrespective of how tracking is accomplished, if the selected target (e.g., target anatomy or interventional tool) moves, the system beamforming controls and signal/image processing are adapted to the new location in accordance with embodiments of the invention. Accordingly, the process of the illustrated embodiment, having tracked the target of interest, returns to block 203 wherein the imaging parameters of system 100 are adapted for imaging the selected target of interest as currently tracked. Thereafter, at block 204, the target imaging mode operates to provide an updated target volume image dataset using the updated imaging parameters.

Although embodiments have been described herein with reference to ultrasound systems, survey imaging modes and target imaging modes in accordance with the concepts of the present invention may be implemented with respect to imaging targets in various imaging systems. For example, the concepts of the present invention may be applied with respect to MRI, CT, PET, Angiographies and other, even non-medical, applications.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An ultrasound imaging system comprising:
an ultrasound transducer;
a processor operable under control of an instruction set to generate images using information acquired by the ultrasound transducer, wherein the processor is configured to
generate a survey image from a survey volume image data set;
receive an indication of an item of interest in the survey image;
adjust one or more imaging parameters based on the indicated item of interest; and
generate a target image from a target volume image data set that is obtained with the one or more adjusted imaging parameters,
wherein the one or more adjusted imaging parameters cause the target image to cover only the indicated item of interest.

2. The system of claim 1, wherein an adjusted imaging parameter includes a transmit focus.

3. The system of claim 1, wherein an adjusted imaging parameter includes a focal depth.

4. The system of claim 1, wherein an adjusted imaging parameter includes an increased beam density.

5. The system of claim 1, wherein an adjusted imaging parameter includes a wobbling angle.

6. The system of claim 1, wherein an adjusted imaging parameter narrows a field of view of the target volume image data set compared with the sample volume image data set.

7. An ultrasound imaging system comprising:
an ultrasound transducer;
a processor operable under control of an instruction set to generate images using information acquired by the ultrasound transducer, wherein the processor is configured to
generate a survey image from a survey volume image data set;
receive an indication of an item of interest in the survey image;
adjust one or more imaging parameters based on the indicated item of interest; and
generate a target image from a target volume image data set volume set that is obtained with the one or more adjusted imaging parameters, wherein the one or more adjusted imaging parameters cause the target image to center the identified item of interest in the target image.

8. The system of claim 7, wherein an adjusted imaging parameter includes a transmit focus.

9. The system of claim 7, wherein an adjusted imaging parameter includes a focal depth.

10. The system of claim 7, wherein an adjusted imaging parameter includes an increased beam density.

11. The system of claim 7, wherein an adjusted imaging parameter includes a wobbling angle.

12. The system of claim 7, an adjusted imaging parameter narrows a field of view of the target volume image data set compared with the sample volume image data set.

* * * * *